(12) United States Patent
Lintner

(10) Patent No.: US 7,182,963 B2
(45) Date of Patent: Feb. 27, 2007

(54) COSMETIC AND DERMOPHARMACEUTICAL COMPOSITIONS FOR SKIN PRONE TO ACNE

(75) Inventor: Karl Lintner, Rambouillet (FR)

(73) Assignee: Sederma (FR)

( * ) Notice: Subject to any disclaimer, the term of this patent is extended or adjusted under 35 U.S.C. 154(b) by 0 days.

(21) Appl. No.: 10/817,670

(22) Filed: Apr. 2, 2004

(65) Prior Publication Data

US 2004/0254245 A1    Dec. 16, 2004

Related U.S. Application Data

(63) Continuation-in-part of application No. PCT/FR02/03344, filed on Oct. 1, 2002.

(30) Foreign Application Priority Data

Oct. 3, 2001    (FR)    ................... 01 12802

(51) Int. Cl.
    *A61K 36/00*    (2006.01)
(52) U.S. Cl. ...................... 424/725; 514/560
(58) Field of Classification Search ............... None
    See application file for complete search history.

(56) References Cited

U.S. PATENT DOCUMENTS

| | | | |
|---|---|---|---|
| 5,723,139 A | 3/1998 | Granger et al. | |
| 6,238,678 B1 * | 5/2001 | Oblong et al. | ............... 424/401 |
| 6,492,326 B1 | 12/2002 | Robinson et al. | |
| 2001/0029266 A1 | 10/2001 | Leroy et al. | |
| 2002/0176903 A1 * | 11/2002 | Kuno et al. | ................. 424/777 |
| 2003/0087789 A1 | 5/2003 | Scheffler | |

FOREIGN PATENT DOCUMENTS

| | | |
|---|---|---|
| DE | 100 15 353 | 10/2001 |
| EP | 0 297 733 | 1/1989 |
| EP | 1 129 697 | 9/2001 |
| FR | 2 785 804 | 5/2000 |
| JP | 04 173739 | 6/1992 |
| JP | 09 118611 | 9/1997 |
| WO | WO-01/17523 | 3/2001 |

OTHER PUBLICATIONS

Giner-Larza et al. "Oleanonic acid, a 3-oxotriterpene from *Pistacia*, inhibits leukotriene synthesis and has anti-inflammatory activity," Eur. J. Pharmacol. 428 (2001) 137-43.
Manez et al., "Effect of selected triterpenoids on chronic dermal inflammation," Eur. J. Pharmacol. 334 (1997) 103-05.
Jie Liu, "Phamacology of oleanolic acid and ursolic acid," J. Ethnopharm. 49 (1995) 57-68.
"Oil based cosmetic products extracted from olive leaves," Chemical Abstracts & Indees vol. 66, No. 26, Jun. 26, 1967 p. 11041.

* cited by examiner

*Primary Examiner*—Christopher Tate
*Assistant Examiner*—S. B. McCormick-Ewoldt
(74) *Attorney, Agent, or Firm*—Lerner, David, Littenberg, Krumholz & Mentlik, LLP

(57) ABSTRACT

The invention relates to the use of an extract of olive leaves (*Olea europaea*) which is titrated in oleanolic acid and which may or may not be associated with a *Larrea divaricata* extract which is titrated in nordihydroguaiaretic acid (NDGA). Said products are intended for all types of cosmetic and dermopharmaceutical compositions for all forms of skin care, for moisturizing and anti-inflammatory purposes and, in particular, for the prevention and treatment of skin prone to acne.

16 Claims, No Drawings

COSMETIC AND DERMOPHARMACEUTICAL COMPOSITIONS FOR SKIN PRONE TO ACNE

CROSS REFERENCE TO RELATED APPLICATIONS

This application is a continuation-in-part of PCT Patent Application No. PCT/FR 02/03344, designating the U.S., filed Oct. 1, 2002, which was published in French, which claims priority from French Patent Application No. FR 01/12802, filed Oct. 3, 2001, the disclosure of which is incorporated herein by reference.

BACKGROUND OF THE INVENTION

Various forms of acne exist. These include: juvenile, which may emerge as of age 9 years, with no premonitory sign of puberty, and which affects approximately 70% of adolescents of both genders; adult, which, outside of the consequences of hormonal contraceptive treatment, corresponds, in fact, in most cases, to juvenile acne persisting in the absence of treatment of after inappropriate treatment; drug-related, the main causes of which are vitamin B12, systemic or local corticosteroids, iodine- or bromine-based preparations, androgens and androgenic progestogen contraceptive pills; neonatal, due to maternal androgens, and for which recovery is spontaneous; excoriated, of young girls, which is an exacerbation of normal and classic juvenile acne due to almost obsessive touching of acne spots.

Thus, most forms of acne derive more or less directly from juvenile acne. Acne is, in all likelihood, a multifactorial disease which can be summarized by the following triad: hyperseborrhea+disorder of keratinization of the pilosebaceous canal+a microbial factor.

Hyperseborrhea

There is no acne without hyperseborrhea and, broadly speaking, acne is proportional to the degree of seborrhea. Sebum secretion is under hormonal control and constitutes one of the best indicators of androgen levels explaining the emergence of acne at the time of puberty, during which a physiological hormonal explosion occurs.

The androgen hormone most involved in acne is testosterone. Gonadal testosterone circulates in the body in a protein-bound form and only free testosterone enters the target cell: the sebaceous gland. There, an enzyme, 5α-reductase, converts testosterone to its metabolite, dihydrotestosterone (DHT), which stimulates the synthesis of nuclear proteins. The more DHT which reaches the nucleus, the greater the increase in sebaceous gland size and proliferation. The glands fill with lipids and, since the sebaceous gland is a holocrine secretory gland, the greater the quantity of excreted sebum.

Keratinization Disorder of the Pilosebaceous Canal

This point constitutes a sine qua non condition for the occurrence of acne. The epithelium bordering the pilosebaceous canal at infra-infundibulum level then forms a large quantity of abnormally keratinized cells, a large quantity of keratin and a particularly sparingly soluble intercellular ground substance. At infra-infundibulum level, this creates a compact plug which prevents expulsion of the sebum: this is the microcyst or closed comedo stage, the true elementary lesion of acne. The microcyst can then evolve in 2 ways: either the keratin and sebum continue to provoke swelling of the microcyst forcing dilation of the acro-infundibulum, thus forming an open comedo or common blackhead, with no real seriousness; or the wall of the microcyst ruptures with irruption into the dermis of sebum, keratin and free fatty acids. An inflammatory reaction occurs, which is exacerbated by the last component in the etiology of acne.

Microbial Factor

Normally, in the pilosebaceous follicle, 3 types of microorganism exist: a yeast: *Pityrosporum ovale*, whose pathogenic role in acne appears nil, a non-pathogenic white *Staphylococcus*, an anaerobic bacteria, diphtheroid and Gram-positive: *Corynebacterium* acnes (formerly called *Propionibacterium* acnes), which synthesizes a lipase able to hydrolyze the triglycerides of sebum into free fatty acids that are irritants for the dermis. This microorganism is also involved in the local production of protease, hyaluronidase and neuraminidase, which exacerbate the inflammatory process cited above.

The data presented above are derived from a review of the following documents: F. Poli (1996): Acné prépubertaire, Le Concours Médical, 118:905–908; P. Morel (1981), polycopié de dermato et vénéro, Le Kremlin Bicêtre: 161–179; Francois Daniel (1977): Dermatologie pratique, Edition Dupuy-Compton Medical, Neuilly. Both during adolescence and adulthood, acne induces a negative self-image in people who have acne-prone skin. The cosmetic industry is thus within its scope when it proposes a new approach to resolving the problems of acne-prone skins.

SUMMARY OF THE INVENTION

The present invention includes the use of oleanolic acid, pure or isolated or contained in titrated olive tree (*Olea europaea*) leaf extract in an effective and/or sufficient quantity, in a cosmetic or dermopharmaceutical composition. These compositions may be intended to prevent and treat the symptoms of acne, hyperseborrhea and acne-prone skin. The oleanolic acid, whether as part of an extract or otherwise may be used along with an effective and/or sufficient quantity of nordihydroguaiaretic acid (pure or isolated or in the form of a titrated *Larrea divaricata* extract).

Cosmetic or dermopharmaceutical compositions intended to prevent and treat the symptoms of acne, hyperseborrhea and to prevent symptoms in acne-prone skin containing an effective and sufficient quantity of oleanolic acid or titrated *Olea europaea* leaf extract containing it. These cosmetic or dermopharmaceutical compositions may also contain an effective and/or sufficient quantity of nordihydroguaiaretic acid or a titrated *Larrea divaricata* extract containing it. In a preferred embodiment of these cosmetic or dermopharmaceutical compositions, the quantity of oleanolic acid is between 1 and 10,000 ppm (0.0001 and 1% m/m), preferably between 10 and 1000 ppm (0.001 and 0.1% m/m). The quantity of nordihydroguaiaretic acid is, if present, between 1 and 10,000 ppm (0.0001 and 1% m/m), preferably between 10 and 1000 ppm (0.001 and 0.1% m/m).

A particularly preferred cosmetic and/or dermopharmaceutical composition includes a concentration of the oleanolic acid (used pure or in the form of *Olea europaea* extract) of between 5 and 50 ppm (0.0005 to 0.05% m/m) and a concentration of nordihydroguaiaretic acid (used pure or in the form of titrated *Larrea divaricata* extract) of between 1 and 100 ppm (0.0001 to 0.01% m/m).

Cosmetic or dermopharmaceutical compositions may include any other ingredient usually employed in the fields of cosmetics and dermopharmacy. These can include, without limitation, lipids including extracted and/or synthetic lipids, gelling and viscosifying polymers, surfactants and emulsifying agents, any water- or fat-soluble active substance, plant extracts of all sorts, synthetic peptides, proteins, vitamins, tissue extracts, marine extracts, sunscreens and antioxidants. A particularly preferred composition includes OSMOCIDE® (marketed by the Sederma company, France). These cosmetic or dermopharmaceutical compositions may be combined with other active substances and may be used in any pharmaceutical form employed in cosmetics or dermopharmacy such as, without limitation, gels, O/W and W/O emulsions, milks, lotions, ointments, scalp lotions, shampoos, soaps, sticks and pencils, sprays and body oils.

The active substances may be used in the form of a solution, dispersion or emulsion, or encapsulated in carriers such as macro-, micro- or nanocapsules, liposomes or chylomicrons, or included in macro-, micro- or nanoparticles, or in microsponges, or adsorbed on powdered organic polymers, talcs, bentonites and other inorganic carriers.

Oleanolic acid, pure or in the form of titrated olive tree (*Olea europaea*) leaf extract, alone or in combination with nordihydroguaiaretic acid (pure or in the form of titrated *Larrea divaricata* extract), or combined with other active substances can be used for the preparation of a medicinal product used for any form of moisturizing or anti-inflammatory care of the skin and in the prevention and treatment of acne-prone skin.

The cosmetic or dermopharmaceutical compositions of the invention may have the active substances impregnated on any sort of textile, synthetic or natural fiber, wool or any material liable to be used for the manufacture of clothing or underclothing, active materials of any sort, wipes, patches, compresses, cottons, cotton buds, dressings, makeup-removal sponges, masks and any other carrier liable to come into direct contact with the skin or scalp to enable continuous topical delivery.

DETAILED DESCRIPTION

It has been discovered that oleanolic acid and extracts of olive tree (*Olea europaea*) leaves titrated with respect to oleanolic acid content, are endowed with a strong inhibitory action on the enzyme, $5\alpha$-reductase, and thus constitute an important component in the treatment of the symptoms of acne-prone skin. It has also been discovered that oleanolic acid and the extracts of olive tree leaves are endowed with antimicrobial activity against *Corynebacterium* acnes and *Acinetobacter calcoaceticus*. The use of oleanolic acid and olive leaf extracts to prevent and treat the symptoms of acne and acne-prone skin is thus new.

In addition, surprisingly, it has been discovered that a synergy is obtained by combining nordihydroguaiaretic acid or an extract of *Larrea divaricata* of known nordihydroguaiaretic acid content with oleanolic acid or extracts of olive tree leaves.

Nordihydroguaiaretic acid is an inhibitor of protein metabolism in the Golgi apparatus and thus plays a moderating role in cell growth. The use of nordihydroguaiaretic acid to slow the growth of the skin and appendages has been described in FR 2785804. It appears that combination of oleanolic acid and nordihydroguaiaretic acid or extracts containing those compounds strengthens the antimicrobial activity and decreases hyperkeratinization concomitantly, thus enhancing prevention of the symptoms of acne.

Anti-acne activity can be further reinforced if the cosmetic and dermopharmaceutical compositions containing said extracts are formulated with other appropriate compounds such as keratolytic, sebum-regulating, moisturizing and/or osmotic active substances (particularly those with specific antimicrobial and anti-inflammatory activities).

The other constituents of the compositions may be any habitually or newly used or usable ingredient in cosmetics and dermopharmacy.

Oleanolic acid combined or not combined with nordihydroguaiaretic acid and/or the plant extracts containing them may thus be advantageously used in the prevention and treatment of acne-prone skin since: oleanolic acid decreases hyperseborrhea by inhibiting $5\alpha$-reductase and nordihydroguaiaretic acid (NDGA) exerts an anti-inflammatory and antiproliferative effect on keratinocytes and reduces hyperkeratinization.

In cosmetic or dermopharmaceutical compositions, it may be advantageous to combine the extracts cited with other active substances in order to strengthen their effect by an additive or synergistic effect of the various products or in order to combine the effect described in this patent application with another beneficial physiological effect for the skin, mucous membranes, cutaneous appendages (hair and scalp), such as OSMOCIDE® (Sederma).

The oleanolic acid and, possibly, nordihydroguaiaretic acid concentrations in the cosmetic or dermopharmaceutical product may vary from 1 to 10,000 ppm (0.0001 and 1%, m/m), preferably between 10 and 1000 ppm (0.001 and 0.1% m/m). In combination with nordihydroguaiaretic acid, preferably 5 to 50 ppm (0.0005 to 0.05% m/m) of oleanolic acid and 1 to 100 ppm (0.0001 to 0.01% m/m) of nordihydroguaiaretic acid will be used. The concentrations of the more or less crude or purified extracts of olive tree leaves and *L. divaricata* used in the finished products depend on their respective oleanolic acid and nordihydroguaiaretic acid contents. The final concentrations of the main active substances (oleanolic acid and nordihydroguaiaretic acid) are to lie within the ranges cited.

Oleanolic acid pure or in the form of titrated olive tree (*Olea europaea*) leaf extract, alone or in combination with nordihydroguaiaretic acid (pure or in the form of titrated *Larrea divaricata* extract) or combined with other active substances, may be used in any pharmaceutical form employed in cosmetics or dermopharmacy: O/W and W/O emulsions, milks, lotions, ointments, scalp lotions, shampoos, soaps, sticks and pencils, sprays and body oils, without that list being exhaustive.

Oleanolic acid pure or in the form of titrated olive tree (*Olea europaea*) leaf extract, alone or in combination with nordihydroguaiaretic acid (pure or in the form of titrated *Larrea divaricata* extract), or combined with other active substances, may be used in the form of solutions, dispersions and emulsions, or encapsulated in carriers such as macro-, micro- or nanocapsules and liposomes or chylomicrons, or included in macro-, micro- or nanoparticles or in microsponges, or adsorbed on powdered organic polymers, talcs, bentonites or other inorganic carriers.

Oleanolic acid pure or in the form of titrated olive tree (*Olea europaea*) leaf extract, alone or in combination with nordihydroguaiaretic acid (pure or in the form of titrated *Larrea divaricata* extract) may be combined with any other usually employed ingredient: extracted and/or synthetic lipids, gelling and viscosifying polymers, surfactants and emulsifying agents, all water- and fat-soluble active substances, plant extracts of any sort, synthetic peptides, proteins, vitamins, tissue extracts, marine extracts, sunscreens and antioxidants.

Oleanolic acid pure or in the form of titrated olive tree (*Olea europaea*) leaf extract, alone or in combination with nordihydroguaiaretic acid (pure or in the form of titrated

*Larrea divaricata* extract) or combined with other active substances, may be used in cosmetic or dermopharmaceutical compositions for all skin care, moisturizing or anti-inflammatory, and in the prevention and treatment of acne-prone skin.

Oleanolic acid pure or in the form of titrated olive tree (*Olea europaea*) leaf extract, alone or in combination with nordihydroguaiaretic acid (pure or in the form of titrated *Larrea divaricata* extract) or combined with other active substances, may be incorporated in cosmetic compositions or dermopharmaceuticals for the preparation of medicinal products used in moisturizing or anti-inflammatory care of the skin and in the prevention and treatment of acne-prone skin.

Oleanolic acid, pure or in the form of titrated olive tree (*Olea europaea*) leaf extract, alone or in combination with nordihydroguaiaretic acid (pure or in the form of titrated *Larrea divaricata* extract), or combined with other active substances, may be used to impregnate any sort of textile, synthetic or natural fibers, wool or any materials liable to be used for the manufacture of clothing or underclothing, active materials of any sort, wipes, patches, compresses, cottons, and cotton buds, dressings, makeup-removing sponges, masks, or any other carrier liable to come into direct contact with the skin and scalp to enable continuous topical delivery. A more complete list of possible cosmetic compositions and other usually employed ingredients can be found in Robinson et al. U.S. Pat. No. 6,492,326 B1, which issued on Dec. 10, 2002. The text from column 5, line 35 trough column 20, line 52 and column 20, line 61 through column 34, line 11 is hereby incorporated by reference. The text and claims as published of WO 03/028692 published on Apr. 10, 2003 and filed Oct. 1, 2002 as PCT/FR02/03344 are hereby incorporated by reference.

EXAMPLES

The following nonlimiting examples are for the purpose of illustrating some of the uses and advantages of certain embodiments of the present invention. Examples 1 to 4 illustrate the various possibilities for compositions intended for cosmetic or dermopharmaceutical uses containing oleanolic acid and/or nordihydroguaiaretic acid or the corresponding extracts.

Examples 5 to 10 illustrate the effects of those compositions and the synergistic effects observed with combination of the various constituents.

Example 1

Concentrated Mix (Premix) for the Preparation of Anti-Acne Cosmetic Products

| | |
|---|---|
| Butylene glycol | 25.00 |
| Oleanolic acid | 0.03 |
| Nordihydroguaiaretic acid | 0.04 |
| PEG-60 almond glycerides | 10.00 |
| Osmocide ® (Sederma) | 64.93 |

Example 2

Cleansing and Moisturizing Gel for Acne-Prone Skins

| | |
|---|---|
| Carbopol ® 1342 (Goodrich) | 0.3 |
| Propylene glycol | 2 |
| Glycerol | 1 |
| White soft paraffin | 1.5 |
| Cyclomethicone | 6 |
| Cetyl alcohol | 0.5 |
| Lubrajel ® MS (United Guardian) | 10 |
| Triethanolamine | 0.3 |
| Oleanolic acid | 0.0015 |
| Nordihydroguaiaretic acid | 0.002 |
| Osmocide ® (Sederma) | 9.0 |
| Water, preservatives, fragrance | q.s. 100 g |

Example 3

Care Cream for Oily Skins

| | |
|---|---|
| Brij ® 721 (ICI) | 2.4 |
| Volpo ® S72 (Croda) | 2.6 |
| Prostearyl-15 (Croda) | 8.0 |
| Beeswax | 0.5 |
| Abil ® ZP 2434 (Goldschmidt) | 3.0 |
| Propylene glycol | 3.0 |
| Carbopol ® 941 (B.F. Goodrich) | 0.25 |
| Triethanolamine | 0.25 |
| Olea europaea extract | 10.0 |
| Larrea divaricata extract | 5.0 |
| Osmocide ® (Sederma) | 10.0 |
| Water, preservatives, fragrances | q.s. 100 g |

Example 4

Cleansing Lotion

| | |
|---|---|
| Ethanol | 1.0 |
| Propylene glycol | 2.0 |
| Abil ® B8851 (Goldschmidt) | 0.5 |
| Eumulgin ® L (Henkel) | 0.6 |
| Oleanolic acid | 0.05 |
| Water, preservatives, fragrance | q.s. 100 g |

Example 5

Inhibition of 5α-Reductase—Enzymatic Assay—In Vitro

Principle and implementation of the test (adapted from Zy and Zu, 1998):

Testosterone is irreversibly metabolized by 5α-reductase to 5-dehydrotestosterone (5-DHT) in the presence of the cofactor NADPH. The reaction is monitored, at 37° C., by determining, using a spectrophotometer, the reduction in the absorbance of the reaction medium at 340 nm, due to the conversion of NADPH to NADP.

The test thus consists in mixing testosterone, NADPH and the test product or its vehicle alone (control reaction). After 3 minutes to allow the system to equilibrate, the baseline absorbance of the system is determined. Then the reaction is triggered by addition of the enzyme, 5α-reductase. After 10 minutes, a second determination of the absorbance, final absorbance, is conducted. The difference between the two measurements reflects the quantity of NADPH consumed. That quantity is proportional to the quantity of testosterone converted to 5-DHT.

Oleanolic acid and nordihydroguaiaretic acid were tested at various concentrations alone or in combination. Results: the following table shows the percentage inhibition (mean±SEM) observed in 5 independent assays.

| Test product | [c] | % inhibition |
|---|---|---|
| Oleanolic acid | 0.01% | 16.7 ± 1.1% |
|  | 0.03% | 31.7 ± 2.9% |
|  | 0.1% | 56.3 ± 2.6% |
| NDGA | 0.01% | 2.1 ± 1.6% |
|  | 0.04% | 3.7 ± 2.9% |
|  | 0.1% | 3.0 ± 1.9% |
| Oleanolic acid + nordihydroguaiaretic acid | 0.03% 0.04% | 68.3 ± 3.1% |

These results clearly demonstrate that oleanolic acid has a strong inhibitory activity on the enzyme, 5α-reductase, since, under the above experimental conditions, 56% inhibition was observed with only 0.1%. Moreover, this effect is specific since it is concentration-dependent.
Nordihydroguaiaretic acid used alone has no activity in this test.
There is strong synergy between the effects when the 2 products are used in combination, since the inhibition observed (68%) is markedly greater than the sum of the individual effects observed in the same test at the same concentrations, since the sum of the effects is only 35.4%.

Example 6

Inhibition of 5α-Reductase—HPLC Determination—In Vitro

Principle and implementation of the test: the aim of this test was to confirm the previous result but using an HPLC analysis method. Unlike 5-DHT, testosterone absorbs light at the wavelength used (245 nm). The decrease in testosterone peak area (which was characterized under our operating conditions by a retention time of 26 minutes) reflects the reduction of the concentration of the compound in the study medium and thus reflects 5α-reductase activity.

The same type of protocol as in the previous example was used, but instead of determining the absorbances, the reaction media were analyzed by HPLC.

Results: the following table shows the percentage inhibition (mean±SEM) observed in 5 independent assays.

| Test product | [c] | % inhibition |
|---|---|---|
| Oleanolic acid (obtained from olive tree leaves) | 0.01% | 10.9 ± 1.4% |
|  | 0.03% | 25.6 ± 2.0% |
|  | 0.1% | 47.7 ± 3.8% |
| Nordihydroguaiaretic acid (obtained from *L. divaricata*) | 0.01% | 1.2 ± 0.4% |
|  | 0.04% | 1.0 ± 0.9% |
|  | 0.1% | 0.9 ± 0.7% |
| Oleanolic acid + nordihydroguaiaretic acid | 0.03% 0.04% | 61.8 ± 4.2% |

The results clearly show that:
the effects observed in this example are very similar to those observed in the previous example confirming the initial hypothesis;
oleanolic acid is endowed with strong inhibitory activity vis-à-vis the enzyme, 5α-reductase, since, under our experimental conditions, 48% inhibition was observed with only 0.1% oleanolic acid. Nordihydroguaiaretic acid used alone had no activity in this test;
there is patent synergy between the effects when the 2 products are used in combination, since the observed inhibition (61.8%) is markedly greater than the sum of the individual effects observed in the same test at the same concentrations, since the sum of the effects is only 26.6%.

Example 7

Anti-Inflammatory Effect—In Vitro

Principle and test implementation: it is possible to estimate a degree of inflammation by determining the quantity of mediators such as prostaglandins, leukotrienes or interleukins.

In this example, we selected assay of interleukin 6 (IL-6) on normal human fibroblasts (HF) and keratinocytes (HK) in culture following exposure to UV-B irradiation.

Broadly speaking, the cells were cultured in a conventional culture medium (DMEMc+10% FCS) for periods of 24 hours for HF and 1 week for HK. After elimination of the buffer and 2 successive washings with phosphate buffer solution, the cells were exposed to UV-B irradiation at a standardized energy level of 50 mJ.cm$^{-2}$.

The buffer was then rapidly eliminated and replaced by the same culture medium as that used at the start of the experiment, but containing the test extracts at the prerequisite concentrations or DMSO for the control series. After 24 hours, the culture medium was harvested and IL-6 concentration determined using a standard ELISA method.

An additional series was conducted using the same protocol but without UV-B irradiation in order to determine the baseline level and control the stability of the study system. All the assays were conducted in triplicate.

The following table shows the results (mean±SEM of the percentage change vs. the tests conducted without UV radiation exposure) for 5 independent assays.

| Test product | [c] | HF % change | HK % change |
|---|---|---|---|
| Control | — | +439 ± 11% | +450 ± 15% |
| Oleanolic acid | 0.01% | +455 ± 14% | +461 ± 16% |
|  | 0.03% | +437 ± 12% | +444 ± 14% |
|  | 0.1% | +441 ± 18% | +450 ± 14% |
| NDGA | 0.01% | +356 ± 18% | +388 ± 10% |
|  | 0.04% | +155 ± 9% | +201 ± 10% |

-continued

| Test product | [c] | HF % change | HK % change |
|---|---|---|---|
| Oleanolic acid + nordihydroguaiaretic acid | 0.1% 0.03% 0.04% | +87 ± 7% +47 ± 4% | +91 ± 14% +58 ± 4% |

The results clearly show that:

nordihydroguaiaretic acid has a remarkable anti-inflammatory effect on the 2 cell lines studied since, under our experimental conditions (HF and HK), inhibition of 19% (+356 vs. +439%) and 14% (+388 vs. +450%) was observed with a nordihydroguaiaretic acid concentration of only 0.01%. Moreover, the effect was specific, since it was concentration-dependent;

oleanolic acid used alone is devoid of activity in this test;

for the 2 cell lines, there was patent synergy between the effects when the 2 compounds were used in combination, since 90% inhibition (+47 vs. +439%, HF) and 87% inhibition (+58 vs. +450%, HK), respectively, were observed. These inhibitions were markedly greater than the sum of the individual effects observed in the same test at the same concentrations.

Example 8

Antiproliferative Effect on Keratinocytes—In Vitro

Test principle and implementation: since the quantity of DNA is constant for each cell, the determination of the overall quantity of DNA is equivalent to measuring the number of cells used for the determination. This principle enables routine use of more refined but very cumbersome methodologies to be avoided. Various methods have been developed on the basis of this protocol, of which, in particular, that used herein. When bound to DNA with a constant and known stereochemistry, the fluorophore, Hoechst 33258, presents, first, increased fluorescence, but also an emission spectrum shift from 492 to 458 nm. By means of comparison with pre-established sets of standards, the concomitant monitoring of the above 2 parameters enables quantification of the quantity of DNA present in the cell samples studied.

Broadly speaking, normal human keratinocytes (HK) are cultured in a classic culture medium (DMEMc+10% FCS) for 1 week, in the absence of the test product (control series in order to determine the baseline cell proliferation of the system studied) or in the presence of the test products alone or in combination. Fluorophore Hoechst 33258 was added at the end of the protocol before withdrawing cell aliquots for assay. The assays were conducted in triplicate as 3 mutually independent assays.

Results: the following table shows the percentage inhibition (mean±SEM) with respect to the quantities of DNA (and hence the number of cells present, as observed in each of the 5 independent assays).

| Test product | [c] | % inhibition |
|---|---|---|
| Oleanolic acid | 0.01% 0.03% 0.1% | 0.9 ± 1.0% 1.1 ± 1.6% 0.7 ± 0.7% |
| NDGA | 0.01% 0.04% 0.1% | 10.2 ± 1.5% 22.3 ± 1.9% 29.9 ± 1.7% |
| Oleanolic acid + nordihydroguaiaretic acid | 0.03% 0.04% | 41.7 ± 3.4% |

The results clearly show that:

nordihydroguaiaretic acid strongly inhibits keratinocyte proliferation since, under our experimental conditions, 10% inhibition was observed with a concentration of only 0.01% nordihydroguaiaretic acid. Moreover, the effect was specific since it was concentration-dependent;

oleanolic acid used alone was devoid of activity in this test;

there was a patent synergy between the effects when the 2 compounds were used in combination, since the observed inhibition (41.7%) was markedly greater than the sum of the individual effects observed in the same test at the same concentrations, since the sum was only 23.4%.

Example 9

Antibacterial Effect on *Corynebacterium* Acnes—In Vitro

Test Principle and Implementation: 1 mL of the premix in example No. 1 or its constituents at concentrations equivalent to 5% of the premix were incorporated in molten agar medium (BioMérieux) plated in a Petri dish. The dish was stirred to blend the compound in the agar. 10 µL of study bacteria suspension diluted to contain approximately $10^4$ and $10^5$ bacteria/mL was applied to the solid agar at room temperature. The plates were then incubated at 37° C. for 24 and 48 hours and inspected visually.

Five strains, *Corynebacterium minutissimum, Propionibacterium* acnes, *Staphylococcus aureus, Staphylococcus hominis* and *Acinetobacterium calcoaceticus* were studied.

Results: The following table shows the observed antimicrobial activity results for the constituents and their combination in the cosmetic excipient.

Oleanolic acid exerted selective antimicrobial activity against the microorganisms *P. acnes* and *A. calcoaceticus*. Nordihydroguaiaretic acid exerted selective antimicrobial activity against *A. calcoaceticus* and *S. hominis*. OSMOCIDE® exerted selective antimicrobial activity against *S. aureus, S. hominis* and *P. acnes*, while none of the other constituents showed any effect.

The combination of the constituents in the premix in example 1 showed the most complete antimicrobial activity, inactivating all the test microorganisms.

The strains studied are shown in the table as:

| | Strains studied | | | | | | | | | |
|---|---|---|---|---|---|---|---|---|---|---|
| | A | | B | | C | | D | | E | |
| Bacteria/mL | $10^5$ | $10^4$ | $10^5$ | $10^4$ | $10^5$ | $10^4$ | $10^5$ | $10^4$ | $10^5$ | $10^4$ |
| Butylene glycol + oleanolic acid | + | + | + | + | + | + | − | − | − | − |
| Butylene glycol + nordihydroguaiaretic acid | + | + | − | − | + | + | + | − | − | − |
| Butylene glycol + water | + | + | + | + | + | + | + | + | + | + |
| OSMOCIDE | + | + | − | − | − | − | − | − | + | + |
| PEG-60 almond oil + water | + | + | + | + | + | + | + | + | + | + |
| 5% premix No. 1 | − | − | − | − | − | − | − | − | − | − |
| Trichlosan (reference substance) | − | − | − | − | − | − | − | − | − | − |

The results at 24 h (above) were the same as those observed at 48 h.
Key:
'+' = bacterial growth,
'−' = no bacterial growth
Strain A: *Corynebacterium minutissimum*
Strain B: *Staphylococcus hominis*
Strain C: *Staphylococcus aureus*
Strain D: *P. acnes*
Strain E: *Acinetobacterium calcoaceticus*

Example 10

Anti-Acne Effect—In Vivo

The study was conducted in 30 volunteers, with equal numbers of both genders, aged 14 to 20 years, selected for their acne-prone skin, i.e. presenting with at least 2 inflammatory lesions (papules, pustules, nodules) and/or 10 retentive lesions (comedo and microcyst).

The test product, the gel in example No. 2, was applied for 2 months, morning and night, after conventional cleansing of the skin. All other products (topical medication, cosmetic or dermatological products) were prohibited throughout the duration of the study.

The lesions were counted and observed by dermatologists, on the same predetermined area of the facial skin (20 cm²), pre-treatment (T0) and after 30 (T30) and 60 (T60) days of treatment. A significant decrease in the lesions and a marked improvement in the state of the face were observed after the cosmetic treatment. The product did not induce irritation, edema or other signs of poor tolerance.

The invention claimed is:

1. A cosmetic or dermopharmaceutical composition comprising: an effective quantity of oleanolic acid, wherein said effective quantity is between about 1 ppm and about 10,000 ppm and an effective quantity of nordihydroguaiaretic acid, wherein said effective quantity of nordihydroguaiaretic acid is between about 1 and about 10,000 ppm, for the treatment of acne, hyperseborrhea and acne-prone skin.

2. The composition of claim 1, wherein said oleanolic acid is contained in an extract of *Olea europaea* leaf.

3. The composition of claim 1, wherein said quantity of oleanolic acid is between about 10 and about 1,000 ppm.

4. The composition of claim 1, wherein said nordihydroguaiaretic acid is contained in an extract of *Larrea divaricata*.

5. The composition of claim 1, wherein said quantity of nordihydroguaiaretic acid is between about 10 and about 1,000 ppm.

6. The composition of claim 1, further comprising at least one other ingredient employed in the treatment of acne, hyperseborrhea and acne-prone skin.

7. The composition of claim 6, wherein said at least one other ingredient employed in the treatment of acne, hyperseborrhea and acne-prone skin is selected from the group consisting of lipids, gelling polymers, viscosifying polymers, surfactants, emulsifying agents, water soluble active substance, fat soluble active substance, plant extract, synthetic peptides, proteins, vitamins, tissue extracts, marine extracts, sunscreens and antioxidants.

8. The composition of claim 1 provided in the form of a gel, oil/water emulsion, water/oil emulsion, milk, lotion, ointment, scalp lotion, shampoo, soap, stick, pencil, spray or body oil.

9. The composition of claim 1, wherein at least one of said oleanolic acid and said nordihydroguaiaretic acid is used in the form of a solution, dispersion, emulsion, is encapsulated in a carrier, microcapsule, nanocapsule, liposome, or chylomicrom, or included in macroparticles, microparticles, nanoparticles or microsponges, or is adsorbed on a powdered organic polymer, talc, bentonite or inorganic carrier.

10. The composition of claim 1, wherein said oleanolic acid is present in an amount of from about 5 to about 50 ppm and said nordihydroguaiaretic acid is between about 1 and about 100 ppm.

11. The composition of claim 10, further comprising at least one other ingredient employed in the treatment of acne, hyperseborrhea and acne-prone skin.

12. The composition of claim 11, wherein said at least one other ingredient employed in the treatment of acne, hyperseborrhea and acne-prone skin is selected from the group consisting of lipids, gelling polymers, viscosifying polymers, surfactants, emulsifying agents, water soluble active substance, fat soluble active substance, plant extract, synthetic peptides, proteins, vitamins, tissue extracts, marine extracts, sunscreens and antioxidants.

13. The composition of claim 12, provided in the form of a gel, oil/water emulsion, water/oil emulsion, milk, lotion, ointment, scalp lotion, shampoo, soap, stick, pencil, spray or body oil.

14. A cosmetic or dermopharmaceutical composition comprising an effective quantity of oleanolic acid, wherein said effective quantity is between about 1 ppm and about 10,000 ppm and an effective quantity of nordihydroguaiaretic acid wherein said effective quantity of nordihydroguaiaretic acid is between about 1 and about 10,000 ppm, impregnated on a textile, synthetic or natural fiber, wool, wipe, patch compress, cotton, cotton bud, dressing, make-up removal sponge, mask, material useful for the manufacture of clothing or underclothing or other carrier liable to come into direct contact with the skin or scalp to enable continuous topical delivery, and wherein said composition exhibits an inhibitory action on 5α-reductase.

15. The composition of claim 1, wherein composition exhibits an inhibitory action on 5α-reductase.

16. The composition of claim 1, wherein said composition exhibits antimicrobial activity, exerts an anti-inflammatory or antiproliferative effect on keratinocytes or reduces hyperkeratinization.

* * * * *

UNITED STATES PATENT AND TRADEMARK OFFICE
CERTIFICATE OF CORRECTION

PATENT NO. : 7,182,963 B2
APPLICATION NO. : 10/817670
DATED : February 27, 2007
INVENTOR(S) : Karl Lintner Page 1 of 1

It is certified that error appears in the above-identified patent and that said Letters Patent is hereby corrected as shown below:

Column 3, line 41, after "content" delete ",".
Column 3, line 59, after "that" insert --a--.
Column 9, line 44, after "that" insert --are--.
Column 14, line 3, after "wherein" insert --said--.

Signed and Sealed this

Fourth Day of March, 2008

JON W. DUDAS
*Director of the United States Patent and Trademark Office*